(12) United States Patent
Johnson et al.

(10) Patent No.: US 7,935,536 B2
(45) Date of Patent: May 3, 2011

(54) SYSTEM FOR WATER REMOVAL AND SOLVENT EVAPORATION

(75) Inventors: Robert S. Johnson, Hampstead, NH (US); Stephen MacDonald, Hudson, NH (US)

(73) Assignee: HorizonTechnology, Inc., Salem, NH (US)

( * ) Notice: Subject to any disclaimer, the term of this patent is extended or adjusted under 35 U.S.C. 154(b) by 822 days.

(21) Appl. No.: 11/190,513

(22) Filed: Jul. 27, 2005

(65) Prior Publication Data

US 2007/0026380 A1 Feb. 1, 2007

(51) Int. Cl.
*C12Q 1/00* (2006.01)

(52) U.S. Cl. ...... 436/174; 435/4; 435/287.1; 435/283.1; 422/68.1; 422/50

(58) Field of Classification Search .................. 436/174; 422/68.1, 50; 210/650; 435/4, 287.1, 283.1; 219/201, 200
See application file for complete search history.

(56) References Cited

U.S. PATENT DOCUMENTS

| | | | |
|---|---|---|---|
| 4,311,594 A * | 1/1982 | Perry | 210/640 |
| 4,875,980 A | 10/1989 | Arita et al. | |
| 5,100,623 A | 3/1992 | Friswell | 422/68.1 |
| 5,268,150 A * | 12/1993 | Burkitt | 422/102 |
| 5,271,846 A * | 12/1993 | Uragami et al. | 210/640 |
| 5,569,357 A | 10/1996 | Kuhn et al. | |
| 6,749,755 B2 | 6/2004 | Johnson | 210/650 |
| 2002/0179529 A1 * | 12/2002 | Johnson | 210/637 |

FOREIGN PATENT DOCUMENTS

WO WO 02/02211 1/2002

OTHER PUBLICATIONS

International Search Report and Written Opinion as issued in corresponding PCT patent application No. PCT/US 06/29233.

* cited by examiner

*Primary Examiner* — Walter D Griffin
*Assistant Examiner* — Christine T Mui
(74) *Attorney, Agent, or Firm* — Grossman, Tucker, Perreault & Pfleger, PLLC

(57) ABSTRACT

An apparatus and method for separating residual water from a solvent and removing a solvent. The apparatus may be sealed and automated. The method comprises providing a solution comprising solvent and residual water and an analyte. The solution may be passed through a membrane to reduce water content wherein an analyte is present at a first concentration. This then may be followed by removing solvent from the solution.

21 Claims, 1 Drawing Sheet

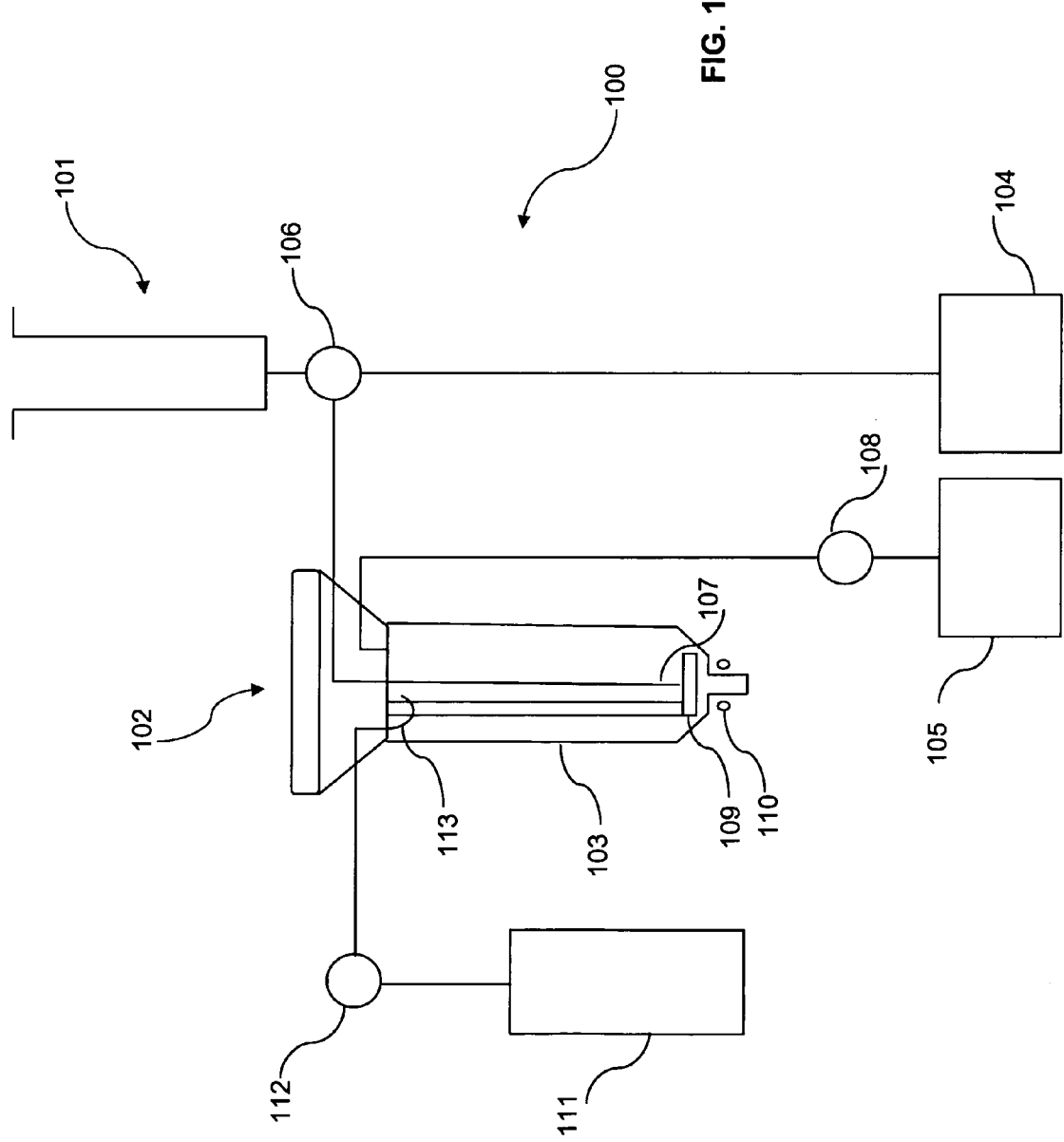

SYSTEM FOR WATER REMOVAL AND SOLVENT EVAPORATION

FIELD OF THE INVENTION

This invention generally relates to the field of chemical laboratory equipment for sample preparation and particularly to the combination of water removal and solvent evaporation. Such water removal and evaporation may yield a desired concentration of analytes for recovery.

BACKGROUND OF THE INVENTION

When samples need to be analyzed for trace organic compounds, the samples are typically extracted with an organic solvent. Due to selective chemistry, the organic solvents extract organic compounds from the sample. Extracted compounds, referred to as analytes, typically cannot be analyzed until residual water is removed from the solvent and the solvent is evaporated down in volume. Residual water in the solvent should be removed because it may have an adverse effect on compound analysis. The solvent should be evaporated down in volume to ensure the analytes are present in a concentration within the detection range of the analytical instrument used for analysis. The individual processes of extraction, removal of residual water, and evaporation are time consuming and operator dependent, thereby typically providing inconsistent recovery of analytes. Loss of analytes due to continual evaporation in unsealed commercial evaporation units may also contribute to inconsistent analyte recovery.

Accordingly, it is an object of the present invention to improve upon current technologies for analyte concentration and provide a more efficient technique for removal of residual water and evaporation of solvents. More specifically, it is an object of the present invention to provide a method and apparatus to increase the rate of analyte concentration and allow for consistent, high recovery of analytes. The method/apparatus of the present invention may also be combined with a method/apparatus for extraction to further enhance the rapid concentration of analytes with consistent, high analyte recovery.

SUMMARY OF THE INVENTION

In a first exemplary embodiment the present invention is directed at a method of removing water and concentrating an analyte in a solvent. This method includes first providing a solution comprising solvent and residual water and an analyte. The solution may then be passed through a membrane to reduce water content wherein the analyte is present at a first concentration. This may be followed by removal of solvent from the solution to provide an analyte at a second concentration which is greater than analyte first concentration.

In a second exemplary embodiment the present invention is directed at an apparatus for removing water and concentrating an analyte in a solvent comprising a reservoir for containing a first solution of solvent, residual water and an analyte. The reservoir may have an opening to drain from the reservoir. A hydrophobic membrane layer may be supplied comprising fluoropolymer material, where the membrane layer may be positioned in series with the reservoir opening. A vessel may be supplied for containing a second solution passed through the membrane and a device may be included for introducing a flow of gas or vacuum into the second solution.

BRIEF DESCRIPTION OF THE DRAWING

FIG. 1 is a sectional view of a concentrator apparatus in accordance with the present invention.

The above and other objects, features, and advantages of the present invention will be apparent in the following detailed description thereof when read in conjunction with the appended drawing wherein the same reference numerals denote the same or similar parts on the figure.

DETAILED DESCRIPTION OF THE DRAWING AND PREFERRED EMBODIMENTS

Referring to FIG. 1, there is illustrated generally an exemplary concentrator apparatus 100. The concentrator apparatus 100 may comprise a separator apparatus 101 for separation of residual water from solvent and an evaporator apparatus 102 for evaporation of solvent.

Separator apparatus 101 may include a reservoir initially containing a solution comprising solvent and residual water and an analyte, the reservoir having an opening to drain from the reservoir, and a hydrophobic membrane layer comprising fluoropolymer material positioned in series with the reservoir opening. The solution may be an extraction solution.

The membrane may comprise two layers of fluoropolymer material, wherein the membrane layers may be characterized as follows:
  Pore Size: 0.05 to 0.2 micron;
  Bubble Point: Individual between 15.0 psi and 23.0 psi (47 mm membrane; isopropanol at 21° C.);
  Water Entry Pressure: 50.0 psi minimum individual;
  Gurley Number: Mean less than or equal to 30.0 seconds;
  Thickness: 1.0-20 mils.

In accordance with the present invention, the following definitions may apply to the above characteristics:

Bubble point: The minimum pressure in $kg/cm^2$ required to force air through the material that has been prewetted with water, isopropanol (IPA), or methanol.

Water entry pressure: The pressure at which water permeates through the membrane. This is a visual test.

Gurley number: A measure of the air permeability of the material. The Gurley number is the time in seconds required for 100 cc of air to pass through a one square inch area of membrane, when a constant pressure of 4.88 inches of water is applied.

The membrane may comprise one layer of fluoropolymer material. In such embodiment, the fluoropolymer membrane may be selected from an expanded fluoropolymer membrane, where an expanded fluoropolymer may be characterized by one or more of the following properties:
  IPA Bubble Point: Greater than or equal to 25 psi, preferably 28.8 psi;
  Alcohol Flow: 60-70 seconds (100 mls of isopropanol at 27.5" Hg through a 47 mm disk);
  Water Entry Pressure: 100 psi.

It should be understood that, while possible embodiments of single and double fluoropolymer membranes have been described in detail herein, the present invention is not so limited.

The step of separating residual water from the solvent may reduce residual water content to less than or equal to 1.0 ppm. The present invention, however, is not limited to such and applies to any solution that may be evaporated/concentrated.

Evaporator apparatus 102 may comprise a vessel 103 initially containing a solution comprising solvent and an analyte, wherein some residual water may be present in the solution. The solution may be an extraction solution. The device 104 may introduce a flow of gas into the solution. The device 105 may generate a vacuum within vessel 103. The flow of gas may enter the solution through valve 106 and gas sparging line 107. The vacuum may be generated in vessel 103 by the opening of valve 108 to vacuum source 105. Evaporator apparatus 102 may include a heater 109. A sensor 110, such as an optical sensor, may monitor the level of the solution.

The vessel 103 may be sealed to atmospheric pressure. Vessel 103 may be made of glass and designed to emulate the traditional KD (Kudema-Danish) method, which is considered one exemplary benchmark for evaporation. Vessel 103 may vary in size and/or quantity, such that analyte concentration may be performed on a variety of extraction sample sizes, for example, LLE (Liquid-Liquid Extraction) or SPE (Solid Phase Extraction). Vessel 103 may be maintained at ambient room temperature during the evaporation process.

The flow of gas into vessel 103 may comprise nitrogen gas. The vacuum generated in vessel 103 may be a relatively low level vacuum. In accordance with the present invention, a low level vacuum may be one in which the pressure ranges from about 5 inches of mercury at the start of the evaporation process to about 20 inches of mercury toward the end of the evaporation process, including all increments therebetween at 1 inch of mercury variation. The vacuum may be varied within said range of about 5-20 inches of mercury at any time during the evaporation process.

Fluid transfer lines comprising microbore PTFE tubing may be used to connect various components of the present invention.

The following non-limiting example is set forth to demonstrate the method of analyte concentration by one embodiment of the present invention as shown in FIG. 1.

Solution comprising solvent and residual water and an analyte may be initially contained in the reservoir of separator apparatus 101. Initially, valve 108 may be closed to vacuum source 105 and valve 106 may be closed to the gas source 104.

Valve 108 may be opened, therein generating a vacuum in vessel 103 by vacuum source 105. The vacuum may decrease the pressure in vessel 103 relative to separator apparatus 101. The solution comprising solvent and residual water and an analyte may pass through the membrane layer in separator apparatus 101, wherein the membrane layer may resist the flow of the solution therein removing water from the solvent. The residual water content may be reduced to less than or equal to 1.0 ppm.

When all of the solvent has passed through the membrane, the solution comprising solvent and an analyte present at a first concentration, wherein some residual water may be present in the solution, may pass through gas sparging line 107 and into vessel 103. Valve 106 may be opened to the gas source 104, therein allowing gas to sweep through gas sparging line 107 and transfer solution remaining in gas sparging line 107 into vessel 103.

Gas continues to flow through gas sparging line 107 and into the solution comprising solvent and an analyte, wherein some residual water may be present in the solution. Gas may be introduced near the bottom of vessel 103. The gas may agitate and mix the solution, therein preventing analytes from sticking to the surfaces of vessel 103 and possibly contributing to the consistent and high analyte recovery observed with the present invention. The gas may also bubble through the solvent, which may therefore increase the surface area of the solvent. Solvent vapor that may be rapidly formed may be removed from vessel 103 by vacuum source 105. The vacuum and flow of gas may provide a synergistic effect which may allow for the rapid evaporation of the solvent, therein contributing to consistent, high recovery of analytes.

Heater 109 may be used in conjunction with the gas and vacuum to further increase the rate of solvent evaporation. Heater 109 may be an internal immersion heater which may heat the solution from a location inside of vessel 103. The heater may be kept on until the solvent level reaches the top of the heater. An internal thermocouple may be used to sense the level of the boiling solvent and turn the heater off before the heater coils are exposed. The use of the heater in conjunction with the sealed evaporation unit may induce a solvent condensation to form inside of vessel 103, therein contributing to the prevention of analyte loss.

Solvent condensation may cause analytes to be present on the inner surfaces of vessel 103. An automatic solvent rinse may wash the analytes from the inner surfaces of vessel 103 and return the analytes to the liquid solvent. A rinse solvent 111 may be introduced into vessel 103 by activating valve 112 and entering vessel 103 through solvent rinse hook 113. The automatic solvent rinse may occur at various stages of the evaporation process, such as when the heater turns off, when the solvent level reaches the sensor, when a heater timer expires, or a combination of the above. The solvent rinse may also be activated manually at any time during the evaporation process.

During the final stages of the evaporation process, the gas flow may be gently introduced onto the surface of the solvent, therein enhancing the recovery of the more volatile compounds. During a final gas sparge stage, the use of a heater may provide a controllable, relatively low level of heat to the solvent, therein contributing to both the rapid evaporation rate and analyte recovery. An optical end point detection system 110 may monitor the level of solution in vessel 103 throughout the evaporation process. When the level of solution drops below gas sparging line 107, the optical end point detection system may signal for the closing of valves 106 and 108 to the gas and vacuum sources. This may prevent additional evaporation and/or analyte loss.

Additional optical sensors may be used to sense the presence of vessel 103. Such additional optical sensors may prevent evaporator apparatus 102 from operating in the absence of vessel 103.

At the conclusion of the evaporation process, an analyte may be present in vessel 103 in a second concentration, wherein the analyte second concentration is greater than the analyte first concentration. A solvent volume of about 0.1-3.0 ml may remain in the analyte second concentration. Preferably, about 0.9 ml of solvent remains in analyte second concentration.

The above described process of analyte concentration by removal of water and solvent evaporation may be automatic or programmed to occur and represents a significant time advantage over previous techniques. Accordingly, the process may be controlled by a processor configured to implement all of the above referenced steps including the removal of water to controlled levels and the automated steps of solvent evaporation and concentration of analyte to some targeted value. The process of analyte concentration may also provide consistent, high analyte yields.

It should be understood that, while the present invention has been described in detail in the example herein, the invention can be embodied otherwise without departing from the principles thereof, and such other embodiments are meant to come within the scope of the present invention as defined in the following claims.

What is claimed is:

1. A method of removing water and concentrating an analyte in a solvent comprising:
   providing a separator apparatus containing a solution comprising solvent and residual water and an analyte;
   passing said solution through a hydrophobic porous membrane of said separator apparatus as a liquid, said porous membrane having a pore size of 0.05 to 0.2 microns to reduce the water content to less than or equal to 1.0 ppm and wherein said analyte is present at a first concentration;

transferring said solution from said separator apparatus to an evaporator apparatus in a fluid transfer line;

removing solvent from said solution to provide said analyte at a second concentration which is greater than analyte first concentration;

wherein the step of removing solvent from said solution to provide an analyte at a second concentration which is greater than analyte first concentration comprises:

introducing a flow of gas into said solution such that the gas bubbles through the solution and mixes said solution to reduce analyte collecting on a surface of said evaporator apparatus;

introducing a vacuum within said evaporator apparatus comprising a vessel containing said solution; and forming solvent vapor and removing said solvent vapor.

2. The method of claim 1 wherein the step of providing a separator apparatus containing a solution comprising solvent and residual water and an analyte comprises:

providing a sample comprising an analyte;

providing a solvent comprising residual water;

extracting an analyte from said sample with said solvent comprising residual water.

3. The method of claim 1 wherein the step of passing said solution through a hydrophobic porous membrane of said separator apparatus as a liquid, said porous membrane having a pore size of 0.05 to 0.2 microns to reduce water content to less than or equal to 1.0 ppm and wherein said analyte is present at a first concentration comprises:

providing a reservoir of said separator apparatus containing a solution comprising solvent and residual water and an analyte, the reservoir having an opening to drain from the reservoir;

resisting the flow of said solution from said reservoir with said hydrophobic porous membrane layer comprising fluoropolymer material, said membrane layer positioned in series with said opening;

passing said solution through said membrane layer and removing residual water from a solvent.

4. The method of claim 1 wherein said membrane comprises a material having an IPA Bubble Point of greater than or equal to 25 psi.

5. The method of claim 1 wherein said vessel is sealed from atmospheric pressure.

6. The method of claim 1 wherein said vacuum is varied.

7. The method of claim 1 including the step of heating said solution.

8. The method of claim 7 including an internal immersion heater.

9. The method of claim 7 including a thermocouple.

10. The method of claim 1 including providing an optical sensor.

11. The method of claim 1 wherein solvent removal results in solvent volume of about 0.1-3.0 ml remaining in said analyte second concentration.

12. The method of claim 1 including an automatic solvent rinse.

13. An apparatus for removing water and concentrating an analyte in a solvent comprising:

a separator apparatus comprising a reservoir for containing a first solution of solvent, residual water and an analyte, the reservoir having an opening to drain from the reservoir;

a hydrophobic porous membrane layer having a pore size of 0.05 to 0.2 microns to reduce the water content to less than or equal to 1.0 ppm and comprising fluoropolymer material, said membrane layer positioned in series with said opening and configured for said solution to pass through said membrane as a liquid;

a fluid transfer line to transfer said solution from said separator apparatus to an evaporator apparatus;

a vessel of said evaporator apparatus for containing a second solution passed through said membrane;

a device for introducing a flow of gas into said second solution such that the gas from said device bubbles through the second solution and mixes said solution and reduces analyte collecting on a surface of said evaporator apparatus.

14. The apparatus of claim 13 wherein said solution comprising solvent and residual water and an analyte is an extraction solution.

15. The apparatus of claim 13 wherein said membrane comprises a material having an IPA Bubble Point of greater than or equal to 25 psi.

16. The apparatus of claim 13 wherein said vessel is sealed from atmospheric pressure.

17. The apparatus of claim 13 including a heater.

18. The apparatus of claim 17 including an internal immersion heater.

19. The apparatus of claim 17 including a thermocouple.

20. The apparatus of claim 13 including an optical sensor.

21. The apparatus of claim 13 including an automatic solvent rinse.

* * * * *

UNITED STATES PATENT AND TRADEMARK OFFICE
CERTIFICATE OF CORRECTION

| | |
|---|---|
| PATENT NO. | : 7,935,536 B2 |
| APPLICATION NO. | : 11/190513 |
| DATED | : May 3, 2011 |
| INVENTOR(S) | : Robert S. Johnson et al. |

Page 1 of 1

It is certified that error appears in the above-identified patent and that said Letters Patent is hereby corrected as shown below:

On the Cover Page, item (73), in Assignee, in column 1, line 1, delete "HorizonTechnology, Inc.," and insert -- Horizon Technology, Inc., --, therefor.

In column 6, line 3, in Claim 8, delete "claim 7" and insert -- claim 5 --, therefor.

In column 6, line 5, in Claim 9, delete "claim 7" and insert -- claim 5 --, therefor.

Signed and Sealed this
Twenty-fifth Day of October, 2011

David J. Kappos
*Director of the United States Patent and Trademark Office*